United States Patent
Kennett et al.

(10) Patent No.: US 6,387,095 B1
(45) Date of Patent: *May 14, 2002

(54) SURGICAL DEVICE COMPRISING A RADIALLY EXPANDABLE NON-CONDUCTIVE SHEATH

(76) Inventors: Loren R. Kennett; Vickie L. Kennett, both of 772 E. 1030 S., St. George, UT (US) 84790-5650

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/020,367

(22) Filed: Feb. 9, 1998

(51) Int. Cl.$^7$ ............................................. A61B 18/18
(52) U.S. Cl. ...................... 606/49; 606/41; 606/167; 606/185; 604/264
(58) Field of Search ........................ 606/41, 49, 108, 606/129, 185, 167; 604/264

(56) References Cited

U.S. PATENT DOCUMENTS

| | | | | |
|---|---|---|---|---|
| 4,253,467 A | * | 3/1981 | Frazier | 606/108 |
| 4,894,059 A | | 1/1990 | Larsen et al. | 604/349 |
| 5,112,330 A | * | 5/1992 | Nishigaki et al. | 606/46 |
| 5,147,400 A | | 9/1992 | Kaplan et al. | 623/13 |
| 5,151,102 A | | 9/1992 | Kamiyama et al. | 606/51 |
| 5,217,458 A | | 6/1993 | Parins | 606/48 |
| 5,250,033 A | | 10/1993 | Evans et al. | 604/160 |
| 5,320,611 A | | 6/1994 | Bonutti et al. | 604/264 |
| 5,383,876 A | | 1/1995 | Nardella | 606/49 |
| 5,445,646 A | | 8/1995 | Euteneuer et al. | 606/198 |
| 5,454,365 A | | 10/1995 | Bonutti | 600/204 |
| 5,484,418 A | | 1/1996 | Quiachon et al. | 604/167 |
| 5,653,697 A | | 8/1997 | Quiachon et al. | 604/280 |
| 5,674,241 A | | 10/1997 | Bley et al. | 606/198 |
| 5,728,103 A | * | 3/1998 | Picha et al. | 606/108 |
| 5,746,694 A | | 5/1998 | Wilk et al. | 600/123 |
| 5,827,227 A | | 10/1998 | DeLago | 604/104 |
| 5,827,296 A | * | 10/1998 | Morris et al. | 606/129 |
| 5,916,145 A | | 6/1999 | Chu et al. | 600/121 |
| 5,935,122 A | | 8/1999 | Fourkas et al. | 604/523 |
| 5,961,499 A | | 10/1999 | Bonutti et al. | 604/272 |
| 5,968,070 A | | 10/1999 | Bley et al. | 606/198 |
| 5,971,938 A | | 10/1999 | Hart et al. | 600/562 |
| 6,019,777 A | | 2/2000 | Mackenzie | 606/198 |
| 6,019,785 A | | 2/2000 | Strecker | 623/1 |
| 6,041,679 A | | 3/2000 | Slater et al. | 76/104.1 |

FOREIGN PATENT DOCUMENTS

| | | | |
|---|---|---|---|
| WO | WO 88/02624 | 4/1988 | A61F/5/453 |
| WO | WO 96/25897 | 8/1996 | A61F/2/06 |
| WO | WO 98/29029 | 7/1998 | A61B/1/00 |
| WO | WO 99/06094 | 2/1999 | A61M/25/00 |

* cited by examiner

Primary Examiner—Linda C. M. Dvorak
Assistant Examiner—R. Kearney

(57) ABSTRACT

A medical instrument apparatus for forming and enlarging percutaneous penetrations comprising an elongate dilation tube (expandable sheath), silicone insert and 12' polyvinyl coated copper wire. The expandable sheath is radially expandable from a small diameter configuration to a large diameter configuration capable of receiving an external stationary tube, for example, a debriding apparatus. The external stationary tube contacts a metal tab housed in the silicone insert which is attached to the 12' electrical cord, allowing an electrical current to pass down the external stationary metal tube thereby becoming the cauterizing instrument to coagulate hemorrhage in the operative field (joint).

41 Claims, 1 Drawing Sheet

SURGICAL DEVICE COMPRISING A RADIALLY EXPANDABLE NON-CONDUCTIVE SHEATH

BACKGROUND—FIELD OF INVENTION

This invention relates to a surgical procedure specifically joint procedures involving arthroscopy, i.e. Knee and shoulder.

BACKGROUND—DESCRIPTION OF PRIOR ART

Physicians practicing surgical procedures known as "Arthroscopy", must insert a cannula for an Arthroscope. Attached to the Arthroscope is a camera that projects an image to a monitor. Examination of the joint; knee, shoulder, ankle or wrist, is performed and decision is made to repair or remove any pathological problem associated with or in the joint. An egress drain is then established so the joint may be filled with fluid, Sorbitol® or Glycine®, creating a working field. Depending on what pathological problem is presented during examination, the necessity may arise to "shave", "bur" or evacuate the joint to repair the pathological problem.

An Arthroscopic Shaver or Bur commonly referred to as a "Soft-tissue Cutter" is employed to cut, trim or burr damaged cartilage, degenerate bone or damaged tendons and/or tissue.

A tourniquet is applied to the upper thigh to reduce bleeding in the knee, ankle or foot, upper arm to reduce bleeding in the elbow or wrist, but cannot be employed during shoulder arthroscopic procedures. Debriding the joint (any joint) may cause bleeding. Current means of coagulating bleeding in the joint is time consuming and inconvenient to a physician with a patient under anesthesia. Coagulation is achieved by removing the debriding apparatus (shaver or bur), re-entering the joint with an elongated probe, hooked at a 90° angle at the working end, attaching that probe to an electro-cautery machine, irritating the joint to visualize the point of bleeding, and touching the bleeding area with the electrified elongated probe. When the hemorrhage has been abated, the elongated probe is removed, the debriding apparatus (shaver or bur) is replaced, the joint is again irrigated and the surgical procedure is resumed. If hemorrhaging occurs again the process is repeated until the hemorrhaging has ceased and the procedure can be completed.

Utilizing this method of coagulation is effective, but inconvenient, time consuming and potentially damaging. A patient under the influence of anesthetics is at risk and any and all time saving measures are necessary to decrease the related health risks of being under anesthesia. The inconvenience of removing the debriding apparatus, irrigating the joint and re-entering the joint with another instrument is time consuming and potentially dangerous to the welfare of the joint. Damage to tissue, tendons, bone and cartilage may occur upon re-entry of either the probe or debriding apparatus (shaver or bur). Each time either apparatus is removed and re-entered more time elapses and the patient is subjected to increased anesthesia time and associated risks of being under the influence of anesthetic drugs and gases.

OBJECTS AND ADVANTAGES

Objects and advantages of the Arthroscopic Cautery Sheath invention are:

(a) provide a single entry point for debridement and cauterization of bleeding during arthroscopic procedures.

(b) to decrease medical costs both in time and supplies:
 (1) time: not having to exit and re-enter the joint with each apparatus accomplishing surgical repair and or coagulation with the same instrument
 (2) supplies: the sheath houses both the debriding and coagulation apparats.

(c) to decrease surgical and anesthesia time for the patient undergoing an arthroscopic procedure.

(d) to provide a safe and effective means of coagulation of hemorrhaging during arthroscopic surgery.

(e) to provide the physician with a competence of being able to debride, irrigate and coagulate during a surgical arthroscopic procedure without exiting and re-entering the joint multiple times.

Further objects and advantages are to provide an instrument which is user friendly and convenient for the physician's use during arthroscopic surgical procedures. The electrical current delivered from the electro-cautery machine is delivered down the external stationary metal tube of the debriding instrument(shaver or bur). The current can then be directed at the hemorrhage site without having to exit the joint or interrupt the surgical procedure by changing instrumentation. Manufacturing costs are minimal and the instrument is totally disposable following arthrosocpic surgical procedures. Single patient use prevents patients from risk of cross-contamination.

DRAWING FIGURES

In the drawings, related figures have alphabetic suffixes.

SUMMARY

In accordance with the present invention, an Anthroscopic Cautery Sheath comprises a radially expandable sheath, silicone insert housing a metal tab and a 12' monopolar cord.

DESCRIPTION

Figure 1A:
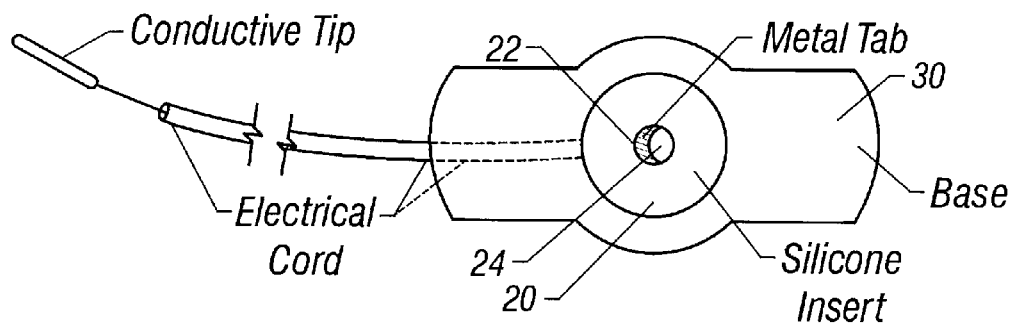
FIG. 1A shows a top view of the instrument including the base and insert.
Figure 1B:
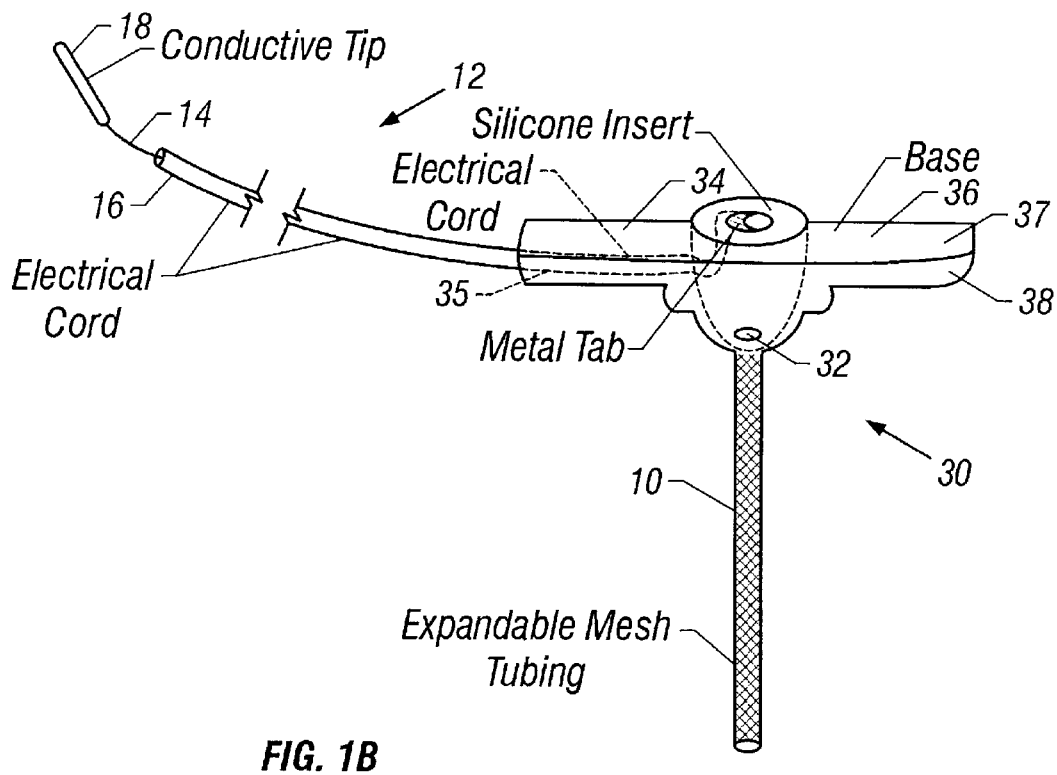
FIG. 1B shows a longitudinal view of all component parts
 (a) expandable sheath
 (b) 12' Monopolar cord
 (c) metal conductor clip
 (d) silicone insert
 (e) base of instrument
Figure 2:
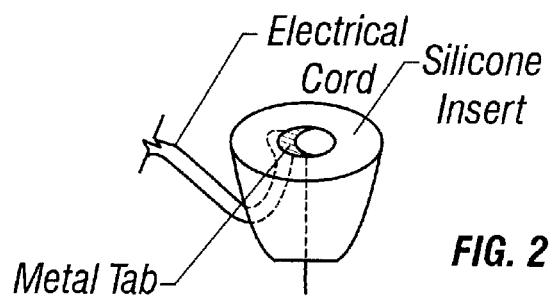
FIG. 2 shows the silicone insert with related component parts
 (a) silicone insert
 (b) metal tab

A typical embodiment of the disclosure of the present invention is illustrated in FIGS. 1A, 1B, and FIG. 2. The expandable sheath 10 comprises a lumen and is 10.5 cm long, constructed of flexible polyethylene fiber and expandable polyvinyl covering. Both coverings are non-conductive. The monopolar cord 12 is a 12' length of copper wire 14 covered with a polyvinyl layer 16. The distal end of the monopolar cord has a metal clip 18 attached to the copper wire 14 which is plugged into an adapter in an electro-cautery machine. The silicone insert 20 houses the metal clip 22 which makes contact with the external metal tube of the debriding instrument (shaver or bur) as it is inserted down the expandable sheath. The base 30 attached to the expandable sheath has an 11 mm diameter opening 32 common with the lumen of the sheath into which the silicone insert is placed. The base has a tapered shape and also comprises an arm 34 that includes an aperture 35 and another arm 36. The base may be separated into an upper piece 37 and a lower piece 38. The silicone insert has an expandable opening 24 3 mm in diameter which accepts the debriding instrument which ranges in diameter from 3.0 mm to 6.0 mm. The base 30 of the expandable sheath is a bivalved polycarbonate resin plastic 6.3 cm in length and 6.0 mm in width. An instrument maybe inserted into the 11 mm opening in the base 30 for surgical use.

Utilizing the Arthroscopic Cautery Sheath is similar to using the sheath for other trocar type surgical procedures. An introducing trocar is used to initially expand the expandable sheath. This expands the sheath to allow the debriding apparatus (shaver or bur) to travel down the length of the sleeve and remain snugly fit to the metal barrel of the debriding apparatus (shaver and bur). The length of the sheath is ideal as it leaves enough working length of the debriding apparatus (shaver or bur) to accomplish debridement of tissue and degenerate bone. The distal tip of the debriding instrument (shaver or bur) will also act as the cauterizing tip to coagulate hemorrhaging in the joint. The debriding apparatus (shaver or bur) can now remain in the operative field joint) and the surgical procedure continues without exit and reentry of two different instruments. This reduces surgical procedure time, anesthesia time, supply expense, operative time expense and patient risk.

Following the conclusion of the operative procedure, the arthroscopic cautery sheath is disposed of as a one-time-use only disposable device.

Conclusion, Ramifications, and Scope

The reader will see that the Arthroscopic Cautery Sheath is a time saving, safe and effective instrument reducing medical expense, operative time, and patient risk while under anesthesia. Beings constructed of disposable material, the instrument becomes safe and effective as one-time-use only instrument, reducing risk of cross-contamination from multiple use arthroscopy instrument sheaths.

The Arthroscopic Cautery Sheath reduces medical expenses by incorporating the cautery apparatus and debriding apparatus (shaver or bur) into a working combination debridement and cauterization instrument.

The Arthroscopic Cautery Sheath reduces operative time, reducing entry and exit of two different instruments in and out of the operative field (joint).

The Arthroscopic Cautery Sheath assists in reducing patient risk by reducing operative time as well as time under anesthesia.

The Arthroscopic Cautery Sheath is made of light-weight polyethylene fibrous material and can be disposed of following a single use.

The Arthroscopic Cautery Sheath is a safe and effective instrument designed to reduce operative time and expense.

The description above contains many specificities and should not be construed as limiting the scope of the invention but as merely providing illustration of some of the presently preferred priorities of this invention.

The scope of the invention should be determined by the appended claims.

What is claimed is:

1. A surgical device for providing a single entry point into an operative field, comprising;
    a radially expandable tubular sheath comprising a non-conductive material;
    a base attached to the radially expandable sheath, wherein the base comprises an opening that is common with the opening of the sheath;
    an insert adapted to be inserted into the base, said insert comprising a conductive metal tab; and
    an electrical cord passing through an aperture in an arm of the base and conductively connected to the metal tab, wherein said metal tab is capable of making contact with a metal tube inserted into the opening of the base.

2. The surgical device of claim 1, wherein the electrically non-conductive material comprises a flexible polyethylene fiber.

3. The surgical device of claim 1, wherein the radially expandable tubular sheath further comprises an expandable polyvinyl covering.

4. The surgical device of claim 1, wherein the radially expandable tubular sheath is about 10.5 cm long.

5. The surgical device of claim 1, wherein the base comprises a resin.

6. The surgical device of claim 5, wherein the resin comprises a polycarbonate resin.

7. The surgical device of claim 1, wherein the base comprises a plastic.

8. The surgical device of claim 1, wherein the base has a tapered shape.

9. The surgical device of claim 1, wherein the base comprises an upper piece and a lower piece.

10. The surgical device of claim 1, wherein the base comprises an arm extending outward from the body of the base.

11. The surgical device of claim 10, wherein the base comprises two arms.

12. The surgical device of claim 1 wherein said insert comprises an opening that is common with the opening of the base and the sheath, and the insert comprises a non-conductive material.

13. The surgical device of claim 12, wherein the insert comprises a silicon material.

14. The surgical device of claim 13, wherein the insert comprises an expandable silicon material.

15. The surgical device of claim 12, wherein the insert comprises an expandable material.

16. The surgical device of claim 15, wherein the expandable lumen of the insert is about 3 mm in diameter.

17. The surgical device of claim 1, further comprising a trocar inserted into the radially expandable tubular sheath.

18. The surgical device of claim 1, further comprising a debriding apparatus inserted into the radially expandable tubular sheath.

19. The surgical device of claim 18, wherein the debriding apparatus comprises a shaver or a bur.

20. The surgical device of claim 18, wherein the debriding apparatus comprises a cauterizing tip.

21. The surgical device of claim 18, wherein the debriding apparatus comprises an external metal tube that makes contact with the conductive metal tab.

22. A surgical device for providing a single entry point into an operative field, comprising:
    a radially expandable tubular sheath comprising a non-conductive material; and
    a base attached to the radially expandable sheath, wherein the base comprises
        an opening that is common with the opening of the sheath,
        an arm extending outward from the body of the base, said arm housing a conductive metal contact.

23. The surgical device of claim 22, wherein the electrically non-conductive material comprises a flexible polyethylene fiber.

24. The surgical device of claim 22, wherein the radially expandable tubular sheath further comprises an expandable polyvinyl covering.

25. The surgical device of claim 22, wherein the radially expandable tubular sheath is about 10.5 cm long.

26. The surgical device of claim 22, wherein the base comprises a resin.

27. The surgical device of claim 26, wherein the resin comprises a polycarbonate resin.

28. The surgical device of claim 22, wherein the base comprises a plastic.

29. The surgical device of claim 22, wherein the base has a tapered shape.

30. The surgical device of claim 22, wherein the base comprises an upper piece and a lower piece.

31. The surgical device of claim 22, wherein the base comprises two arms.

32. The surgical device of claim 22 further comprising an insert, wherein the insert comprises an opening that is common with the opening of the base and the sheath, and the insert comprises a non-conductive material.

33. The surgical device of claim 32, wherein the insert comprises a silicon material.

34. The surgical device of claim 33, wherein the insert comprises an expandable silicon material.

35. The surgical device of claim 32, wherein the insert comprises an expandable material.

36. The surgical device of claim 35, wherein the expandable opening of the insert is about 3 mm in diameter.

37. The surgical device of claim 22, further comprising a trocar inserted into the radially expandable tubular sheath.

38. The surgical device of claim 22, further comprising a debriding apparatus inserted into the radially expandable tubular sheath.

39. The surgical device of claim 38, wherein the debriding apparatus comprises a shaver or a bur.

40. The surgical device of claim 38, wherein the debriding apparatus comprises a cauterizing tip.

41. The surgical device of claim 38, wherein the debriding apparatus comprises an external metal tube that makes contact with the conductive metal tab.

* * * * *